United States Patent

Muni et al.

[11] Patent Number: 5,569,196
[45] Date of Patent: Oct. 29, 1996

[54] TRACKABLE INTRAVASCULAR CATHETER

[75] Inventors: Ketan P. Muni, San Jose; Celso J. Bagaoisan, Newark; Troy L. Thornton, Foster City, all of Calif.

[73] Assignee: Advanced Cardiovascular Systems, Inc., Santa Clara, Calif.

[21] Appl. No.: 272,103

[22] Filed: Jul. 7, 1994

Related U.S. Application Data

[63] Continuation of Ser. No. 918,832, Jul. 21, 1992, abandoned.

[51] Int. Cl.[6] ............................................. A61M 29/00
[52] U.S. Cl. ........................ 604/96; 604/281; 606/194
[58] Field of Search ...................... 138/DIG. 3; 526/247; 128/DIG. 14, 656–658; 606/192–195; 604/96–103, 164, 264–265, 280–282

[56] References Cited

U.S. PATENT DOCUMENTS

| | | | |
|---|---|---|---|
| 4,058,578 | 11/1977 | Kuhls et al. | 526/247 |
| 4,634,432 | 1/1987 | Kocak | 604/282 |
| 4,636,346 | 1/1987 | Gold et al. | 604/280 |
| 4,638,982 | 1/1987 | Powell . | |
| 4,690,175 | 9/1987 | Ouchi et al. | 604/282 |
| 4,739,768 | 4/1988 | Engelson | 128/658 |
| 4,748,805 | 6/1988 | Horzewski et al. . | |
| 4,775,371 | 10/1988 | Mueller, Jr. . | |
| 4,817,613 | 4/1989 | Jaraczewski et al. | 604/282 |
| 4,821,722 | 4/1989 | Miller et al. | 606/192 |
| 4,840,622 | 6/1989 | Hardy | 604/264 |
| 4,848,344 | 7/1989 | Sos et al. | 606/194 |
| 4,917,667 | 4/1990 | Jackson | 604/96 |
| 4,944,745 | 7/1990 | Sogard et al. | 606/194 |
| 4,955,862 | 9/1990 | Sepetka | 128/658 |
| 4,960,410 | 10/1990 | Pinchuk | 606/194 |
| 5,040,548 | 11/1991 | Yock | 606/194 |
| 5,047,045 | 9/1991 | Arney et al. | 606/194 |
| 5,061,273 | 10/1991 | Yock . | |
| 5,074,845 | 12/1991 | Miraki et al. | 606/194 |
| 5,078,702 | 1/1992 | Pomeranz | 128/658 |
| 5,312,356 | 5/1994 | Engelson et al. | 604/282 |
| 5,370,655 | 12/1994 | Burns | 604/96 |

FOREIGN PATENT DOCUMENTS 1618422 1/1991 U.S.S.R. ............................... 604/282

*Primary Examiner*—Randall L. Green
*Assistant Examiner*—Mark Bockelman
*Attorney, Agent, or Firm*—Heller, Ehrman, White & McAuliffe

[57] ABSTRACT

A trackable intravascular catheter having a distal section having a laminated tubular structure with the outer lamina of the tubular structure having a Shore hardness of about 30 to about 80 D and an inner lamina which is diametrically more rigid than the outer lamina. The catheter construction is particularly suitable for over-the-wire coronary angioplasty catheters.

9 Claims, 1 Drawing Sheet

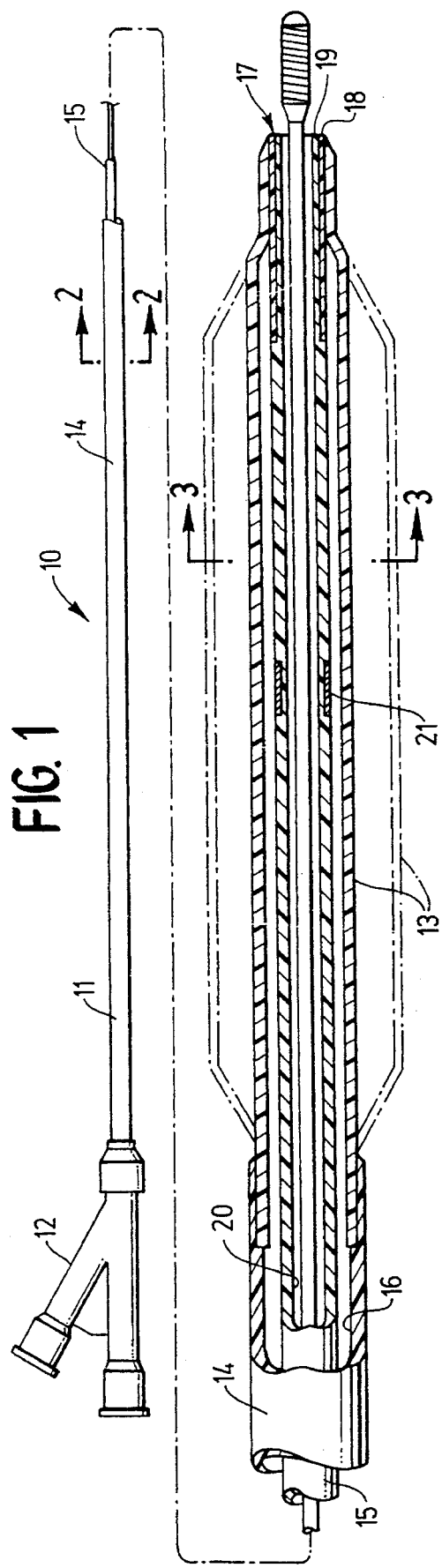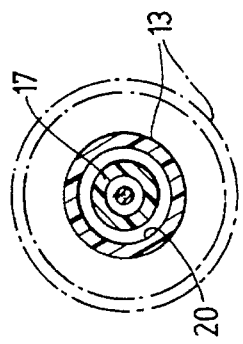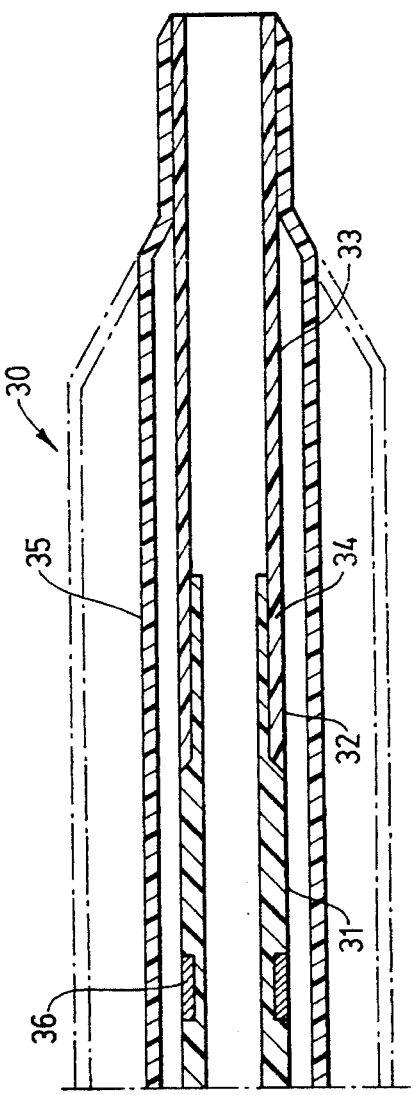

TRACKABLE INTRAVASCULAR CATHETER

This is a continuation of application Ser. No. 07/918,832 which was filed on Jul. 21, 1994, now abandoned.

BACKGROUND OF THE INVENTION

This invention generally relates to catheters suitable for intravascular procedures such as percutaneous transluminal coronary angioplasty (PTCA).

PTCA is a widely used procedure for the treatment of coronary heart disease, wherein a balloon dilatation catheter is advanced into the patient's coronary artery and a relatively inelastic balloon on the distal end of the catheter is inflated within the stenotic region of the patient's artery to open up the arterial passageway and increase the blood flow through the artery.

To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The guiding catheter is advanced within the arterial system until the preshaped distal tip of the guiding catheter is disposed within the aorta adjacent the ostium of the desired coronary artery. The guiding catheter is twisted or torqued from the proximal end, which extends out of the patient, to guide the distal tip of the guiding catheter into the ostium. The balloon dilatation catheter may then be advanced through the guiding catheter into the patient's coronary artery until the balloon on the catheter is disposed within the stenotic region of the patient's artery. The balloon is then inflated to dilatate the stenosis.

One type of dilatation catheter frequently used in PTCA procedures is an over-the-wire type balloon dilatation catheter, such as the SIMPSON ULTRA LOW PROFILE®, the HARTZLER ACX®, the HARTZLER ACX II®, the PINKERTON 0.018™ or the ACS TEN™ balloon dilatation catheter sold by the assignee of the present invention, Advanced Cardiovascular Systems, Inc. (ACS). When using an over-the-wire dilatation catheter, a guidewire is usually inserted into an inner lumen of the catheter before it is introduced into the patient's vascular system and then both are introduced into and advanced through the guiding catheter to its distal tip which is seated within the ostium of the desired coronary artery. The guidewire is first advanced out the seated distal tip of the guiding catheter into the desired coronary artery until the distal end of the guidewire extends beyond the lesion to be dilatated. The dilatation catheter is then advanced out of the distal tip of the guiding catheter into the patient's coronary artery, over the previously advanced guidewire, until the balloon on the distal extremity of the dilatation catheter is properly positioned across the lesion to be dilatated. Once properly positioned across the stenosis, the balloon is inflated one or more times to a predetermined size with radiopaque liquid at relatively high pressures (e.g., generally 4–12 atmospheres) to dilate the stenosed region of a diseased artery. After the dilatation the balloon dilatation catheter is removed from the dilated stenosis and increased rates of blood flow will pass through the dilatated region.

One of the deficiencies noted with dilatation catheters is the difficulty in getting the catheter to track over the guidewire when making sharp turns in tortuous anatomy. The tracking characteristics of a catheter is a function of both the pushability and the flexibility of the catheter shaft. Pushability generally concerns the ability of a catheter to transmit to the distal end of the catheter an axial force applied to the proximal end of the catheter. This characteristic generally relates to the stiffness of the catheter wall or the presence or absence of stiffening elements within the catheter shaft. The greater the stiffness, the greater the pushability. The ease at which the catheter can be advanced over a convoluted guidewire positioned within the patient's artery is a function of its flexibility and particularly the flexibility of the distal extremity of the catheter.

What has been needed and heretofore unavailable is an intravascular catheter which exhibits excellent trackability with little or no loss in pushability. The present invention satisfies this and other needs.

SUMMARY OF THE INVENTION

This invention is directed to intravascular catheters, particularly to dilatation catheters suitable for PTCA, which have excellent trackability and pushability.

The catheter of the invention generally includes an elongated catheter shaft with a guidewire receiving inner lumen extending through the shaft. A distal portion of the catheter shaft has an inner tubular member which defines the guidewire receiving inner lumen extending through the distal portion and which has a laminar construction of inner and outer lamina, with the outer lamina formed of polymer material which is softer and significantly more flexible than the polymer material from which an inner lamina is made. Generally, the thickness of the outer lamina may be about 10 to about 90%, preferably about 30 to about 70%, of the total thickness of the laminar construction including both the inner and outer lamina. Generally, the hardness of the softer outer lamina ranges from about 30 to about 80 D, preferably about 45 to about 50 D (Shore hardness values).

In a presently preferred embodiment the inner lamina is either formed of a lubricous material or the inner lumen adapted to receive a guidewire is provided with a lubricous lining in order to increase the trackability.

The catheter of the invention has been found to track much better than prior dilatation catheters with little or no loss in pushability or guidewire movement. In a tortuous pathway the catheter provides better wire movement than conventional catheters. The catheter also provides better kink resistance and due to the softer distal tip minimizes traumatic engagement with arterial walls. These and other advantages of the invention will become more apparent from the following detailed description thereof when taken in conjunction with the accompanying exemplary drawings.

BRIEF DESCRIPTION OF THE DRAWINGS

FIG. 1 is an elevational view, partially in section, of a dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. I taken along the lines 3—3.

FIG. 4 is an elevational view in section of a distal portion of an alternative embodiment of the invention.

DETAILED DESCRIPTION OF THE INVENTION

Reference is made to FIGS. 1–3 which illustrate a dilatation catheter 10 embodying features of the invention. The dilatation catheter 10 generally includes a catheter shaft 11 with an inflatable member 12 on the distal end of the shaft and an inflatable tubular section 13 on the distal extremity of the catheter. The catheter shaft 11 has an outer tubular member 14 which is provided with the inflatable tubular section 13 and an inner tubular member 15 which is disposed within the outer tubular member 14 and defines with the outer tubular member an annular inflation lumen 16. The annular inflation lumen 16 is adapted to direct inflation fluid from the proximal end of the catheter 10 to the interior of the inflatable section 13 of the catheter.

The distal portion 17 of the inner tubular member 15 has a laminar structure wherein the outer lamina 18 is formed of relatively soft, flexible thermoplastic material and the inner lamina 19 is formed of relatively high strength, diametrically relatively rigid thermoplastic material and is preferably provided with a lubricous inner surface. The inner surface of the inner lamina 19 defines the guidewire receiving inner lumen 20 which extends within the inner tubular member 15 from its proximal to its distal end. The distal end of the inflatable portion 13 is secured by suitable means such as heat bonding or an adhesive, e.g. a cyanoacrylate based adhesive such as Loctite™ 414, to the distal end of the inner tubular member 15 to seal the interior of the inflatable section 13 to prevent the loss of inflation fluid. While not shown in the drawings, a means, such as one or more small passageways, may be provided to vent air from the interior of the inflatable portion but which prevent the passage of inflation liquid. See, for example, the venting systems described in U.S. Pat No. 4,638,805 (Powell) and U.S. Pat No. 4,821,722 (Miller, et al.) which are incorporated herein by reference. A radiopaque marker 21 is provided about the midpoint of the inner tubular member 15 which extends through the interior of the inflatable section 13 to facilitate fluoroscopic observation of the inflatable section when the catheter is disposed within a patient's vascular system. The inflatable section 13 in the inflated condition, as described in the example below, is shown in phantom.

A presently preferred embodiment of the invention, shown in FIGS. 1–3, is an over-the-wire type dilatation catheter for PTCA wherein the outer tubular member 14 has an outer diameter of about 0.02 to about 0.04 inch (0.05 to 0.10 cm), typically about 0.037 inch (0.094 cm), an inner diameter of about 0.015 to about 0.035 inch (0.038 to 0.089 cm), typically about 0.03 inch (0.076 cm). The wall thickness of the outer tubular member 14 can vary from about 0.002 to about 0.008 inch (0.0051 to 0.0201 cm), typically about 0.003 inch (0.0076 cm). The distal inflatable section 13 of the outer tubular member 14 may have an outer diameter of about 0.025 to about 0.030 inch (0.064 to 0.076 cm), typically about 0.027 inch (0.069 cm) and an inner diameter of about 0.020 to about 0.025 inch (0.05 1 to 0.064 cm), typically about 0.023 inch (0.058 cm). The wall thickness will vary depending upon the burst pressure desired but generally will range from about 0.001 to about 0.003 inch (0.0025 to 0.0076 cm). The inner tubular member 15 has an outer diameter of about 0.012 to about 0.016 inch (0.030 to 0.041 cm), typically about 0.014 inch (0.036 cm). The overall length of the catheter 10 may range from about 100 to about 150 cm but is typically about 135 cm. The length of the inflatable section 13 may range from about 1 to about 4 cm, but typically is about 2 cm. The length of the distal section 17 having the laminar structure extends at least about 0.25 to about 40 cm, preferably about 0.4 to about 10 cm. If desired the entire length of the inner tubular member 15 may have the laminar structure.

The catheter components may be formed of conventional materials The outer tubular member may be formed of polyethylene. The inflatable member may be formed of polyethylene, polyethylene terephthalate, polyvinyl chloride or a polyolefinic ionomer such as those sold under the trademark Surlyn® by E.I. dupont, deNemours & Co., e.g., sodium ionomers 8020/IBE, 8920 and 8940, zinc ionomer 9020 and lithium ionomers 7930 and 7940. The inner tubular member proximal to the distal laminated section may be formed of a polyethylene, polyimide and a fluoropolymer such as poly(tetrafluoro)ethylene. In one presently preferred embodiment, the inner lamina is formed of a lubricous material such as a fluoropolymer or is provided with a lubricous inner surface defining the guidewire receiving inner lumen facilitate the advancement of the catheter over the guidewire disposed within the inner lumen. The inner lamina may be conveniently formed of the composite material described in copending be conveniently formed of the composite material described in copending application Ser. No. 07/833,369, filed Feb. 10, 1992, now abandoned entitled COMPOSITE MATERIAL HAVING A LUBRICOUS SURFACE FOR CATHETER USE. The inner lamina may also be formed of thermoplastic fluoropolymers having monomer units selected from the group consisting of —(—$CF_2$—$CF_2$—)— and —(—$CF_2$—CHR—)—, where R is selected from the group consisting of —H, —F, —$CF_3$, —$CH_3$ and —$OCF_3$. At least 4% (by weight) of the monomer units and preferably at least 20% of the monomer units forming the thermoplastic fluoropolymer material should be selected from the aforesaid fluoride monomer units. The thermoplastic fluoropolymer material may be homopolymers or copolymers of such monomer units or blends of homopolymer or copolymer segments formed of the monomer units. Non-fluoride monomer units may be incorporated into the thermoplastic fluoropolymer material, particularly compatible ethylene and methyl methacrylate monomers. The softer flexible outer lamina may be formed of softer grades of polyethylene, e.g. low density or mixed low and high density, or nonirradiated forms of the ionomers mentioned above.

The bonds between the various plastic components may be formed by conventional means such as heat bonding, suitable adhesives and the like. The use of the softer outer lamina eliminates the need to plasma or corona treat the exterior of the inner member in order to facilitate the bonding of the distal end of the balloon to the distal end of the inner tubular member.

In one presently preferred embodiment, the laminated section of the inner tubular member is formed by coextruding the inner and outer lamina or extruding the outer lamina on to a previously formed inner lamina.

FIG. 4 illustrates the distal end of an alternative embodiment of a dilatation catheter 30 of the invention wherein the inner tubular member 31 is provided with an intermediate laminar construction 32 with a relatively soft flexible distal extremity 33. The distal extremity 33 and the outer lamina 34 are preferably formed in a one piece construction as shown in the drawing. The distal end of the inflatable member 35 is secured to the exterior of the distal extremity 33 by a suitable adhesive (not shown) or by thermal means. Radiopaque marker 36 is provided at the mid-point of the inflatable member 35. The remaining details of the catheter are as described previously for the embodiment shown in FIGS. 1–3.

While the invention has been described herein primarily in terms of conventional over-the wire dilatation catheters, those skilled in the art will recognize that the invention can be utilized in other types of dilatation catheters such as rapid exchange type catheters such as described in U.S. Pat. No.

5,040,548 (Yock), U.S Pat. No. 5,061,273 (Yock), and U.S. Pat. No. 4,748,982 (Horzewski, et al.) which are incorporated herein by reference. The invention may also be employed with over-the-wire perfusion catheter, and rapid exchange type catheters having perfusion capabilities such as described in copending application Ser. No. 07/541,264, filed Jun. 19, 1990, now abandoned which is incorporated herein by reference. A variety of modifications can be made without departing from the scope of the invention.

What is claimed is:

1. A dilatation catheter for angioplasty procedures which is readily trackable over a guidewire through a patient's coronary arteries, comprising:

a) an elongated catheter shaft having an inflation lumen and a guidewire receiving lumen extending therein;

b) an inflatable dilatation member on a distal portion of the catheter shaft having an interior in fluid communication with the inflation lumen in the catheter shaft and being formed of a heat bondable polymeric material; and c) wherein the catheter shaft includes a distal tubular extension which defines at least a portion of the guidewire receiving inner lumen extending therein, said distal tubular extension extends through at least a portion of the interior of the inflatable dilatation member and out a distal end thereof, said distal tubular extension having a laminated section formed of a soft outer tubular lamina being formed of a polymeric material secured to an inner tubular plastic lamina diametrically more rigid than the outer tubular plastic lamina, said laminated section having a proximal end located within the inflatable dilation member and a distal end located distal to the inflatable member and a distal portion of said inflatable dilatation member heat bonded to said outer tubular lamina.

2. The dilatation catheter of claim 1 wherein the distal extremity of the elongated shaft has a second tubular member disposed about the tubular portion having the laminated construction.

3. The dilatation catheter of claim 1 wherein the tubular extension distal to the laminated section which is formed of soft polymer material.

4. The dilatation catheter of claim 3 wherein the soft material from which the outer lamina is formed is an olefinic ionomer selected from the group consisting of zinc, sodium and lithium ionomers.

5. The dilatation catheter of claim 1 wherein the outer lamina and the distal extremity are formed into a unitary element.

6. The dilatation catheter of claim 1 wherein the outer lamina has a Shore hardness from about 30 to about 80 D.

7. The dilatation catheter of claim 1 wherein the outer lamina has a Shore hardness from about 45 to about 50 D.

8. The dilatation catheter of claim 1 wherein the inner lamina is formed of from a thermoplastic fluoropolymer selected from the group consisting of homopolymers and copolymers of tetrafluoroethylene and a monomer $-(-CF_2-CHR-)-$, where R is selected from the group consisting of $-H$, $-F$, $-CF_3$, $-CH_3$ and $-OCF_3$, and blends of such homopolymers and copolymers.

9. The dilatation catheter of claim 8 wherein the thermoplastic fluoropolymer includes at least 4% by weight of monomeric units selected from the group consisting of tetrafluoroethylene and a monomer $-(-CF_2-CHR-)-$, where R is selected from the group consisting of $-H$, $-F$, $-CF_3$, $-CH_3$ and $-OCF_3$.

* * * * *